United States Patent [19]

Damadian et al.

[11] Patent Number: 4,770,182
[45] Date of Patent: Sep. 13, 1988

[54] NMR SCREENING METHOD

[75] Inventors: Raymond V. Damadian, Woodbury; Anthony J. Giambalvo, Kings Park; Rajendra K. Shenoy, Commack; Jan V. Votruba, Port Jefferson Station, all of N.Y.

[73] Assignee: Fonar Corporation, Melville, N.Y.

[21] Appl. No.: 935,251

[22] Filed: Nov. 26, 1986

[51] Int. Cl.⁴ ............................................. A61B 5/05
[52] U.S. Cl. .................................. 128/653; 324/309; 324/306
[58] Field of Search ...................... 382/6, 20; 324/307, 324/309, 306; 378/4, 901, 20; 364/415, 414; 128/653, 660

[56] References Cited

U.S. PATENT DOCUMENTS

| | | | |
|---|---|---|---|
| 4,075,700 | 2/1978 | Blay | 382/6 |
| 4,093,859 | 6/1978 | Davis et al. | 378/20 |
| 4,149,247 | 4/1979 | Pavkovich et al. | 382/6 |
| 4,354,499 | 10/1982 | Damadian | 128/653 |
| 4,516,582 | 5/1985 | Redington | 128/653 |
| 4,523,596 | 6/1985 | Macovski | 324/309 |

*Primary Examiner*—Ruth S. Smith
*Attorney, Agent, or Firm*—Lerner, David, Littenberg, Krumholz & Mentlik

[57] ABSTRACT

A medical screening method for examining a patient utilizing NMR techniques is disclosed. The method uses an NMR imaging apparatus which has a scanning volume region of a limited size and which is operative to produce, during the course of a single scanning operation, a collection of spatially encoded NMR image data for a set of volume elements defined by the part of the patient positioned in the scanning volume region. A patient is positioned within the NMR apparatus, the NMR apparatus operated to conduct a scanning operation, and the patient then moved so that an additional volume portion of the patient is positioned within the scanning volume region. The NMR apparatus is then operated to conduct a further scanning operation with respect to the additional volume portion. This procedure of moving the patient and conducting additional scanning operations is continued until substantially the entire body of the patient is scanned and NMR image data collected therefor. An array of selected region elements are selected from the various sets of volume elements so as to define a selected region of the patient which is contained within parts of the different scanned volume portions. A composite image of the patient in the selected region is then produced from the stored collections of NMR image data by utilizing the spatially encoded NMR image data which corresponds to the selected region elements. Such method thus permits a convenient technique for conducting whole body scans of patients in a relatively short period of time.

28 Claims, 5 Drawing Sheets

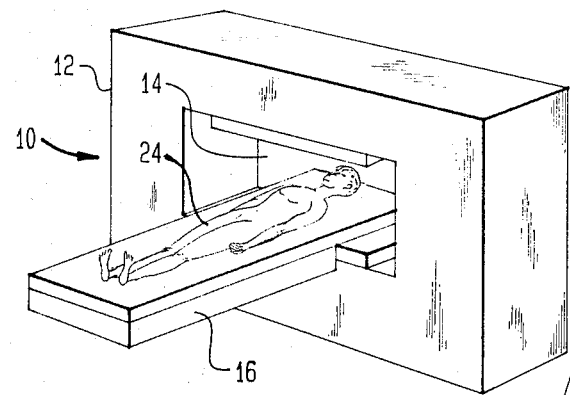
FIG. 1
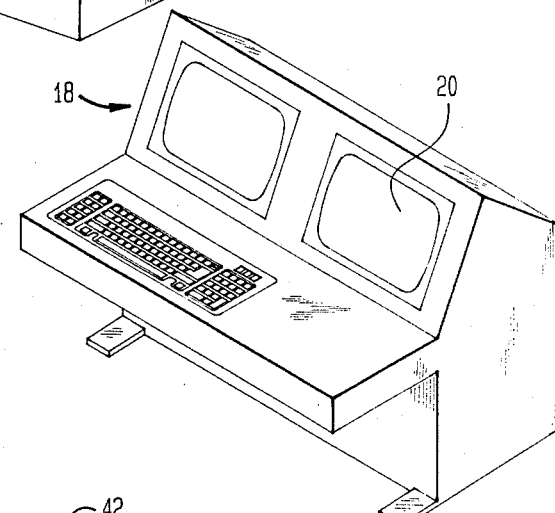
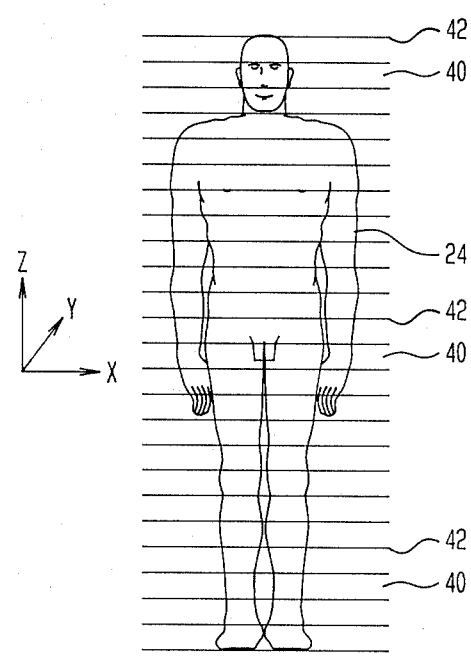
FIG. 2

NMR SCREENING METHOD

FIELD OF THE INVENTION

The present invention is directed to a medical screening method for examining patients, and more particularly, to a medical screening method which enables substantially whole body images to be obtained of patients with an NMR imaging apparatus that may only have a limited scanning region therein.

BACKGROUND OF THE INVENTION

Since Dr. Raymond Damadian first suggested using nuclear magnetic resonance (NMR) techniques for detecting cancer, both in vitro and in vivo, in the early 1970's, the field of NMR scanning and imaging has rapidly developed such that today medical NMR imaging is an accepted and highly useful modality for the detection of various diseases and abnormalities. For instance, NMR imaging, or magnetic resonance imaging (MRI) as it is sometimes known, is known to be useful in the detection of neoplastic diseases (for example, cancer), vascular diseases (for example, aneurisms), degenerative diseases or disorders, traumatic disorders, congenital disorders, inflammatory disorders, and metabolic disorders as well as a number of other disorders or diseases. Indeed, NMR imaging, despite its relative infancy, is now believed to be one of the more powerful medical imaging modalities in terms of its ability to show abnormalities in human tissue and body fluids, even surpassing CT and X-ray imaging methods and techniques in many areas of the body such as the posterior fossa, the spinal cord and many soft tissues. The potential medical usefulness of NMR scanning and imaging is still being investigated and studied, and it is expected that the types of diseases or disorders for which NMR imaging is useful will increase, particularly as new imaging techniques and methods are developed.

Present day NMR scanning and imaging systems include highly sophisticated pieces of equipment. As is known, such equipment includes means for providing a primary static magnetic field of high strength and uniformity in a particular region thereof, as well as means for applying an orthogonally-directed oscillating magnetic field at particular frequencies (usually in the radio frequency or RF range) so as to produce NMR signals from selected nuclei of the patient or person positioned in the apparatus. Present day NMR imaging systems also include means for detecting such produced NMR signals, as well as suitable electronic controls and other equipment, such as computers, for processing of the derived signals to produce spatially encoded NMR image data, and for storing same for the later production of images based thereon. In this regard, with present day NMR imaging systems, the spatially encoded NMR data comprises NMR signal information and spatial information obtained during a scanning operation for a multitude of small volume areas in a selected region of the patient, generally known as small volume elements or voxels. For convenience of physicians and other medical personnel, the spatially encoded NMR data is then displayed in the form of a two-dimensional image or pictorial representation of the particular area of the patient for which the data is collected. In this regard, the images are produced by assigning a particular grey scale or brightness level to the NMR signal information for each of the small areas and then displaying such information in the form of a matrix. Thus, an NMR image is simply a visual translation of the derived NMR signal information obtained during the imaging scan or procedure into a grey scale.

As is well-known, the NMR signal information, generally the intensity or amplitude of the NMR signals measured during the scanning procedure, is a complex function of various tissue-related parameters. These tissue-related parameters generally are the spin-density of the particular nuclei being imaged (usually protons or hydrogen atoms in most medical NMR imaging applications), as well as the spin-lattice relaxation time ($T_1$) and spin-spin relaxation time ($T_2$), the latter two parameters both being exponential time constants which characterize the rate of return to equilibrium of the perturbed nuclei following the application of the perturbing RF or oscillating magnetic field. In this regard, the $T_1$ and $T_2$ information contained in the derived NMR signals is closely related to an indicative of the differences between normal healthy tissue and diseased or abnormal tissue, such that the resulting NMR images can be used by physicians and other medical personnel for the purposes such as might be caused by various types of diseases or disorders such as those noted hereinabove.

Present day NMR imaging techniques generally employ magnetic field gradients for encoding spatial information into the derived NMR signals so that data can be acquired in a relatively rapid manner for a large number of small volume regions or areas of the patient. Generally, with such systems, sets of orthogonal magnetic field gradient coils are provided in the apparatus for generating magnetic field components in the same direction as the static field, but whose strengths vary along the direction of the gradients. The application of such magnetic field gradients serve to change the magnetic field strength within the apparatus at various locations, thus changing the frequency of the applied oscillating magnetic field required for exciting the selected nuclei and/or the frequency of the derived NMR signals. Decoding of the spatially encoded information in the derived signals is then achieved through the use of two-dimensional and three-dimensional Fourier transformation techniques. Numerous such imaging techniques utilizing magnetic field gradients are known in the art, and are generally employed in connection with homogeneous or substantially homogeneous primary static magnetic fields.

With such present day NMR imaging systems, the scanning volume region of the apparatus, i.e. the region from which usable spatially encoded NMR image data is acquired, is of a limited size which is significantly less than the size of patients for which data is to be acquired. More particularly, with present day NMR image systems, NMR imaging data is generally obtained for a thin plane or slice of the patient or, in some instances, a series of thin planar regions stacked one on top of the other. It will thus be appreciated that NMR image data is collected from a three-dimensional array of a large number of small volume elements of particular finite dimensions. For instance, the three-dimensional array may comprise a three-dimensional array of rectangular geometry, in which the length and width is typically on the order of approximately 25"×25", and the thickness or height is on the order of about 12". The two-dimensional NMR images are then produced from the image data for the series or sets of volume elements lying along a particular planar region within the three-dimensional array of rectangular geometry. The number of voxels or volume elements along any particular dimension of the rectangular prism-shaped volume can vary, but typically, may be on the order of either 128 or 256 elements along each edge. The resulting image will thus constitute a matrix having either 128 rows and 128 columns, or 256 rows and 256 columns. The size of the volume elements in plane in present day systems generally is 1 mm, but may vary for 0.5-2 mm. The slice thickness dimensions of the volume elements may vary independently, but typically is from 2-10 mm. Thus, very high resolution images are provided of the parts or regions of the patient for which the data is collected and displayed in the form of an image.

Since the scanning volume region of present day NMR imaging systems is of a limited size, it will be appreciated that in practice today, NMR imaging is used for examining particular localized regions of possible interest in a patient, as opposed to being used for examining the entire or substantially the entire body of the patient. Furthermore, in most instances, physicians only request and obtain NMR images (and only with respect to particular regions of potential interest) when there appears to be some basis for suspecting a particular type or types of disease or illness. In other words, based upon a physician's examination and interview of the patient, as well as the results of other tests which might be conducted on the patient, a physician may develop a number of potential or possible reasons for the patient's symptoms, and thus, order to request that NMR images be obtained in a suspected region or area of the patient. The NMR images are then used by the physician to determine whether particular abnormalities are present which are consistent with particular possible diagnoses, or to rule out certain causes or conditions symptomatic of a particular disease or illness. Thus, NMR images are generally only used with respect to patient's who are not healthy or who are suspected of being no healthy. Further, the NMR images generally are obtained for only particular regions or possible interest and are only used for purposes of determining whether there is any abnormality at the particular region of interest. They are not generally used in the manner of a medical screening or checkup procedure for purposes of screening both the healthy and unhealthy population to hopefully determine, at an early stage, whether the patient has a disease or is developing a condition indicative of disease or illness.

In some instances, NMR images have been used to screen patients who have a high potential risk for a particular disease or abnormality, such as cancer. For instance, NMR imaging may be used with respect to patients exposed to asbestos at some point in their lives, it being realized that such group of people have a high risk for developing cancer. In these instances, the patients may be scanned at intervals during their life to look for the occurrence of particular abnormalities which would be expected if cancer is present or developing. Again, however, the images are only obtained in those areas of the body where the particular type of cancer would be expected, and are only intended for determining whether a particular type of abnormality or condition is present.

Here it should be noted that since NMR imaging techniques do not employ ionizing radiation, such as is employed in X-ray or CT equipment, and have no known harmful effects to the patient, and further, since NMR imaging is known to be useful in detecting abnormalities caused by a vast array of different types of diseases or illnesses, NMR imaging has the potential to be a highly useful screening tool for physicians with respect to all areas of the body, if NMR scans and images could be obtained in a rapid and practical manner for virtually the entire body. To date, however, such total body scanning NMR imaging techniques for acquiring NMR image data in a rapid, practical and useful manner for substantially the entire body of a patient do not exist.

The reason for this is severalfold. First, present day NMR imaging techniques and apparatus are directed to obtaining high resolution images of particular localized regions of the body. Thus, the emphasis in present day developments has mainly been directed to reducing scanning times while, at the same time, obtaining the same or higher resolution images. The resolution capabilities of NMR images are inversely related to the size of the small volume elements for which individual NMR signal information is obtained, i.e., the smaller the volume element, the higher the resolution. Typically, the size of the volume elements for which NMR signal information is obtained is on the order of 3-30 $mm^3$. Typically, NMR images comprise a matrix of $256\times256$ picture elements, or over 65,000 pixels or regions for which NMR image data must be acquired. With the desire to obtain high-resolution images in which the individual volume elements or regions are 3-30 $mm^3$ in size, it will be appreciated that the resulting image will only constitute a display of approximately $10''\times10''$, although NMR images data may be acquired during the course of a scan for a somewhat larger area. With such NMR images, it will be appreciated that the number of images necessary to represent the entire body or substantially the entire body of the patient is very large and cannot practically be reviewed by a physician interested in screening a patient's body.

Another factor leading away from NMR imaging being used in connection with a general screening or checkup-type procedure is the fact that the NMR imaging apparatus presently used has only a limited scanning volume region from which NMR signal information can be obtained. Thus, in order to acquire NMR information with respect to the entire body utilizing present high-resolution imaging techniques, a large number of separate scanning operations would be required for each different region of the body. This, in turn, requires movement of the patient, and also, performing new setup operations for each separate scan. These factors all increase the time for acquiring the overall NMR image data for all areas of the body.

Furthermore, even if the data is acquired for the entire body, the images which are produced are images of only selected regions of the body, namely, regions lying in the different portions of the body for which each separate scanning operation is performed. In other words, while techniques have been developed for acquiring large amounts of NMR imaging data, and in relatively fast scanning times, with present day techniques this is only useful for producing a large number of separate images for each separate region or portion of the body which is scanned. As can be appreciated, with the present day desire to only obtain high-resolution images, the number of regions for which spatially localized NMR imaging data has to be acquired significantly increases such that the number of NMR images required to be reviewed is so great as not to be practical for use by physicians for performing a general screening or checkup-type technique.

Thus, while NMR imaging techniques might be useful in connection with a general medical screening application, such techniques are not presently practical for use in connection with a total or substantially total body scan of a patient. In essence, with present day NMR imaging techniques, the number of NMR images required are so great as not to be practical for use by physicians in performing a general screening or checkup-type procedure, the individual images produced only being representative of selected regions of the patient for which NMR image data is acquired in separate scanning operations and the number of images required for representing the entire or substantially the entire body being very great in number.

SUMMARY OF THE INVENTION

In accordance with the present invention, there is provided a medical screening method for examining a person utilizing NMR techniques. The method of the present invention comprises providing an NMR apparatus of the type having a scanning volume region into which a part of a person to be examined is positioned and also having NMR imaging means operable to produce a collection of spatially encoded NMR image data for a set of volume elements from the part of the person positioned in the scanning volume region. The NMR imaging means is operable to produce the collection of spatially encoded NMR image data relative to the scanning volume region during the course of a single scanning operation. Further, the collection of spatially encoded NMR image data includes both spatial information and NMR signal information for the set of volume elements. A person to be examined is positioned within the NMR apparatus so that the scanning volume region defines a first volume portion of the person having a first set of volume elements. The NMR imaging means is then operated to conduct a scanning operation to produce the collection of NMR image data for the first set of volume elements, the collection of NMR image data then being stored. Thereafter, the person is moved so that the scanning volume region defines at least one additional volume portion of the person having at least one additional set of volume elements, the additional volume portion and additional set of volume elements being different from the first volume portion and first set of volume elements. The operating and storing steps are then repeated for the additional volume portion of the person defined by the scanning volume region so as to produce and store the collection of NMR image data for the additional set of volume elements. These steps of moving the patient and operating the NMR imaging means and storing the collection of NMR image date may be repeated as desired so as to produce and store additional collections of NMR image data for each additional set of volume elements, depending upon the extent to which the person is to be screened. A composite image of the person in a selected region of the person contained within parts of the first and additional volume portions of the person is then produced from the stored collections of NMR image data. The selected region is comprised of an array of selected region elements which are contained in the selected region of the person for which the composite image is to be produced, the selected region elements including volume elements contained in the first set of volume elements and volume elements contained in at least one additional set of volume elements. In this manner, physicians or other medical personnel can use the composite NMR images for determining whether any abnormalities or potential abnormalities exist.

In accordance with a preferred embodiment, additional volume portions of the person, comprised of additional sets of volume elements, are moved into the scanning volume region so the NMR image data can be obtained for substantially the entire body of the person and then displayed in a composite image or images of the patient. Conveniently, each of the composite images may constitute side or front planar images of the person, incorporating parts of the head, neck, chest, torso and/or extremities, taken along different sagittal or coronal planes of the person. In accordance with another preferred embodiment, in which the NMR imaging means is operated so as to produce NMR signal information representative of blood flow, the composite image can display parts of the circulatory system of the person.

With the composite images obtained in accordance with the present invention, in which image data is collected in a number of scanning operations but displayed in a composite format, the number of images which a physician has to review is significantly reduced. The present invention thus provides a practical and useful technique by which a general screen or checkup can be conducted by physicians or other medical personnel. In particular, physicians are not required to wade through a vast number of conventional-type NMR images each having high resolution and each representing only selected small regions of the patient.

In accordance with a preferred embodiment, the size of the individual volume elements for which NMR image data are acquired are somewhat larger than those presently and conventionally used in NMR imaging applications, e.g. the volume elements are of a size of about 2-10 mm. as opposed to 1 mm. or less as with conventional NMR imaging apparatus. Although this results in a lower resolution for the image data obtained in accordance with the present invention, the sacrifice in resolution serves to render the overall medical screening method practical and usable for its intended purpose, namely a screening procedure for examining persons who do not have symptoms indicative of disease or illness, or who are not suspected of being ill. Although the screening procedure could be utilized with respect to persons having particular symptoms or suspected illnesses, generally speaking, for such applications conventional NMR imaging techniques would be employed with respect to particular localized areas of the person. Of course, however, the screening method in accordance with the present invention could still be useful in connection with persons suspected of particular illnesses or having particular symptoms in order to locate particular regions of the person where high-resolution images are to be obtained.

These and further features and characteristics of the present invention will now be discussed with reference to the accompanying drawings which illustrate the preferred embodiments of the present invention.

BRIEF DESCRIPTION OF THE DRAWINGS

FIG. 1 is a perspective view of a conventional NMR imaging apparatus for obtaining spatially localized NMR image data with respect to a part of a person positioned in the apparatus and which may be used in the practice of the method of the present invention.

FIG. 2 is a schematic front view of a person illustrating a plurality of axial planar regions for which NMR image data is to be collected during a plurality scanning operations in accordance with a preferred embodiment of the present invention.

DESCRIPTION OF THE PREFERRED EMBODIMENTS

Figure 3:
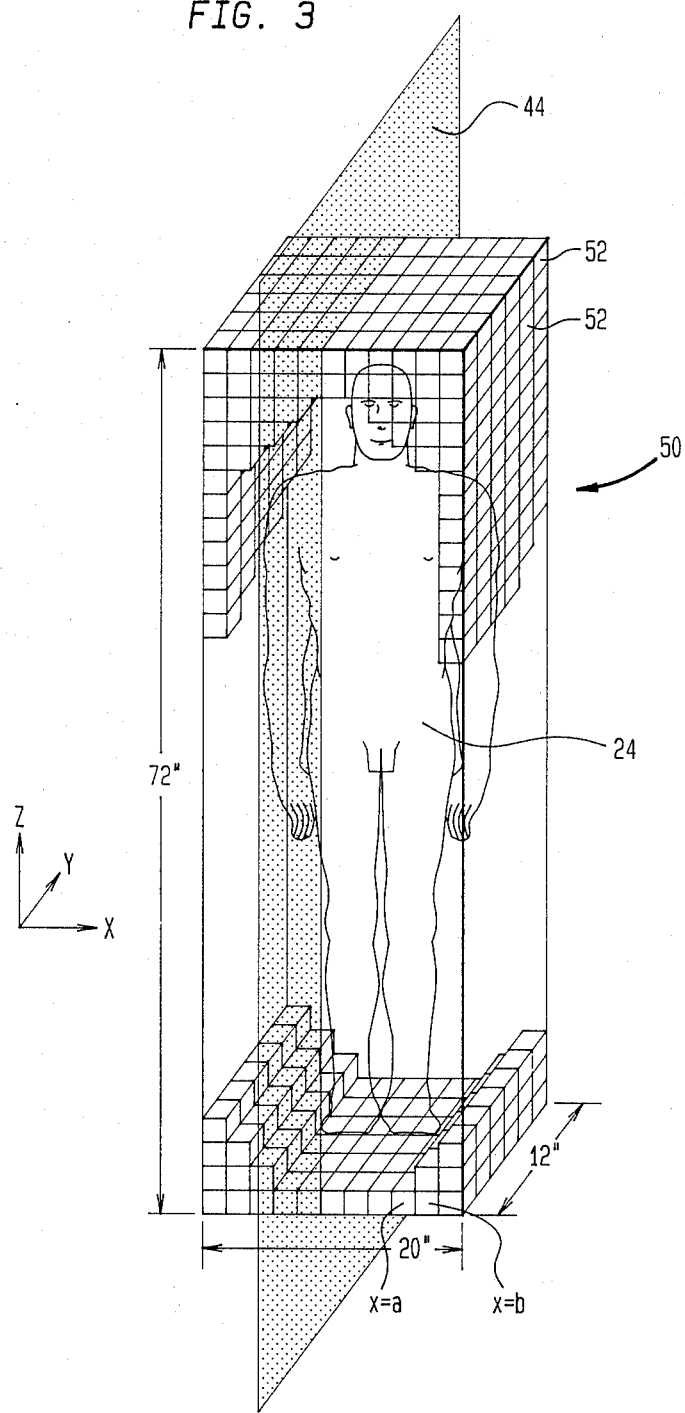
FIG. 3 is a schematic illustration of a three-dimensional array of volume elements for which NMR imaging data is acquired in accordance with a preferred embodiment of the present invention, for purposes of clarity the particular number of volume elements shown being substantially less than those for which data would typically be acquired in order to illustrate the principles in accordance with the method of the present invention.

Referring now to the drawings wherein like reference characters represent like elements, there is shown in FIG. 1 a conventional NMR imaging system 10 of the type for producing a collection of spatially encoded NMR image data for a set of volume elements from a part of a patient or person positioned in a scanning volume region of the apparatus 10. The NMR imaging system 10 includes a frame 12 having an opening 14 therein of sufficient size to accommodate a human form therein and through which a person to be examined is introduced. The frame 12 encloses various components or means (not shown) for producing NMR responses from a selected part of the person positioned therewithin. Such components or means enclosed within the frame 12, as is conventional, comprise means for producing a primary or static magnetic field, an RF transmitting means for producing an oscillating magnetic field, detecting means for detecting produced NMR responses and gradient magnetic field producing means for use in spatially encoding the produced NMR responses. The NMR imaging system 10 also includes means (now shown) for processing the acquired NMR data into images composed of voxels.

The primary or static magnetic field may be produced by means of a permanent magnet system, an electromagnet system, a superconducting magnet system, or a combination of such magnet systems. Preferably, the static magnetic field producing means serves to generate a static, substantially homogeneous, magnetic field of sufficient strength and uniformity or flatness over a relatively large area or volume within a portion of the opening 14 of the frame 12. However, nonuniform magnetic fields could be employed, such as that disclosed, for example, in U.S. Pat. No. 4,354, 499.

Also, as is well-known, the RF transmitting means may comprise a coil or coils through which a radio frequency pulse is applied at a particular frequency or set of frequencies to excite selected nuclei within the static magnetic field. As is known, when the oscillating or RF magnetic field is turned off, the selected nuclei emit or produce an NMR signal which is of the same frequency as that of the applied RF magnetic field and which can be detected by the detecting means. The detecting means may comprise an RF receiver coil, and often is the same coil used as the RF transmitting means.

The gradient magnetic field producing means generally comprise orthogonal sets of coils which in one possible scanning procedure are periodically pulsed on and off during a scanning operation for encoding spatial information into the detected NMR signals or responses. The magnetic field gradient coils each generate a magnetic field component in the same direction as the static field, but their strengths vary along the direction of the gradients so that particular regions within the apparatus 10 have different magnetic field strengths. As the frequency of the oscillating magnetic field for exciting selected nuclei (and of the emitted NMR signals) is dependent upon the strength of the primary or static magnetic field, it will be appreciated that in the presence of a magnetic field gradient, the frequency for exciting selected nuclei and of the received NMR signals will vary. Various techniques have been developed based on the use of magnetic field gradients for thus encoding spatial information into the detected NMR responses obtained during a scanning operation. For example, one such technique, known as spin-warp imaging, is described in the book entitled "Nuclear Magnetic Resonance Imaging in Medicine", published in 1981 by Igaku-Shoin, Ltd., Tokyo.

Imaging techniques based upon magnetic field gradients are generally employed in present day NMR imaging systems as they permit the collection of spatially encoded NMR image data for a multitude of points or small volumes within a selected volumetric region. Conveniently, this region from which spatially encoded NMR imaging data is obtained during a scanning sequence may be termed "the scanning volume region", which constitutes the region in which selected nuclei within the patient's body are simultaneously subjected to the application of the primary or static magnetic field and the oscillating of RF field and from which usable NMR signals, encoded with spatial information, are derived. In conventional NMR imaging systems 10, the scanning volume region is located within a portion of the opening 14 and is significantly smaller in size than the size of the person being examined, such that NMR responses can only be obtained during a single scanning operation from a limited portion of the person's body. Conventionally, the scanning volume region defines a three dimensional space from which usable NMR responses are obtained for a multitude of small volume elements, such as small cubes or rectangular solids, which make up the three-dimensional space. The size of the scanning volume region, and of the small volume elements defined therein, is dependent on the imaging techniques utilized to produce and collect the NMR responses during a scanning operation, as well as on the size of the primary or static magnetic field produced. Typically, the scanning volume region may comprise a cylindrical or rectangular solid volume having a thickness or height of approximately 12", with at least one of the lateral or transverse dimensions being approximately 22". The minimum size of the volume elements in any direction is about 0.5–1 mm.

Conventional NMR imaging techniques have been developed for obtaining NMR imaging data for single or multiple slices within the scanning volume region, as well as for a three-dimensional array of small volume elements. For example, with respect to single-slice acquisition techniques, NMR imaging data is acquired for a slice passing through a portion of the person, with the slice being comprised of a plurality of volume elements of a predetermined thickness and arranged in rows and columns. The NMR image data for the matrix of small volume elements within the slice can then be displayed in the form of a two-dimensional image in which the individual picture or pixel elements of the image represent one of the volume elements within the slice for which NMR data is acquired. The image is formed by assigning a particular grey scale value of brightness for the NMR signal or response for each of the small volume elements within the slice. With conventional NMR imaging techniques, the number of picture elements or pixels in the resulting image, corresponding to the number of volume elements or voxels in the slice for which data is acquired, may typically be on the order of 256×256, or over 65,000. Here it should be noted that each picture element or pixel in the resulting image represents information from a volume element or set of volume elements of the slice.

Multi-slice imaging techniques and three-dimensional volume imaging techniques are also known in which NMR image data is acquired during the course of a single scanning operation for a three-dimensional solid volume comprised of a multiple number of slices stacked one on top of the other. Again, the NMR signals obtained for each of the volume elements within the three-dimensional array represent the NMR responses obtained from small volume regions of the person's body within the three-dimensional solid region. With multi-slice imaging techniques, individual slices are selectively excited by the use of magnetic field gradients and selective RF pulses to obtain the NMR image data, whereas in three-dimensional volume acquisition techniques, individual slices are obtained through processing of the signal information acquired from the entire volume. With either of these techniques, the collection of NMR image data includes NMR signal information for each of the volume elements contained in the three-dimensional solid volume as well as spatial information concerning the location or position of the various volume elements for which the NMR signal information is acquired.

As shown in FIG. 1, the NMR imaging system 10 also includes a table or bed 16 onto which a patient or person 24 lies. The bed or table 16 includes suitable drive means (not shown) for moving the bed 16 into the opening 14 of the frame 12 in order to position the person 24 in a desired position for conducting an NMR data acquisition procedure with respect to the part of the person 24 positioned in the scanning volume region of the apparatus 10. The NMR imaging system 10 also includes an operator's console 18 having suitable controls thereon for controlling proper positioning of the patient bed or table 16, and thus, the person 24 lying thereon, within the scanning volume region, as well as suitable means to enable the operator to input various controls and information for selected data acquisition techniques, setup operations, and other types of operational procedures and controls for conducting a scanning operation. The console 18 also conveniently includes a monitor 20 for displaying images produced from the collected NMR data. Thus, the operator may review at the console 18 a particular image or set of images of the portion of the person arranged in the scanning volume of the apparatus 10.

The NMR imaging system 10 also includes various other hardware and equipment (not shown), such as computers, for use in processing the NMR signal or response information to provide the collection of spatially encoded NMR image data and storing of such data, as well as for producing images therefrom. In this regard, suitable software may also be provided in association with the system 10 for enabling the operator to produce images of particular slices or regions within the scanning volume region for which data has been acquired. For example, if NMR image data is acquired for a three-dimensional solid volume of a part of the person 24, for instance a part of the person's head, software controls are generally provided for enabling the operator to display a transverse or axial slice, a sagittal or side-view slice, or a coronal or front-view slice of the portion of the person's head for which data has been acquired. It is also possible with conventional NMR imaging systems to obtain and display NMR image data along planes which are oblique or angled with respect to the three primary orthogonal axes of the scanning volume region. Such software and/or hardware for processing and storing is conventional and well-known, and therefore, will not be described further herein.

Thus, it will be appreciated that conventional NMR imaging systems provide great flexibility for obtaining particular images along various different slices and at different angles or orientations, but only with respect to the small volume region defined by the scanning volume of the NMR imaging apparatus 10. Thus, with conventional NMR imaging techniques, if a portion of a person's body is positioned in the scanning volume, NMR imaging data is only acquired for a part of the body, such as the head, and NMR images can only be displayed or obtained with respect to a particular plane contained within the volumetric region of the person 24 defined by the scanning volume. While it is possible with conventional NMR imaging apparatus to reposition the person and conduct additional scanning operations, to thereby acquire NMR image data for a different volumetric portion of the part of the person, again, such collected NMR image data can only be displayed for a particular slice or plane lying within such other region. This greatly limits the ability of a physician or other medical personnel to conduct a medical screening procedure of a patient, particularly if the screening procedure were to be performed with respect to the entire or substantially the entire body of the patient. As NMR imaging data from which images can be produced is only acquired and displayed for relatively small volumetric regions of the patient, the number of images which would have to be viewed by the physician are so great as to not be practical in connection with performing an examination or screening process with respect to the entire or substantially the entire body of the patient.

For instance, in conventional NMR imaging systems, the volume elements for which individual NMR imaging signals and information are obtained are generally on the order of 3–30 $mm^3$ in size. Considering axial slices of 5 millimeters in thickness, a six-foot tall patient would require acquisition of image data for over 360 different slices, thus requiring a physician to review and consider over 360 different image slices to perform a full screening operation of a patient. Furthermore, with multi-slicing imaging techniques in which data for on the order of 20 slices can be acquired in about four minutes in a single scanning operation, the number of scanning operations which would have to be performed to scan the entire body would still take over 1 hour simply to acquire the data. Still further, although a number of new NMR imaging techniques have been developed for acquiring NMR image data for slices and three-dimensional volumetric arrays in a rapid manner, particularly in comparison to data acquisition times for conventional techniques (for example, gradient or field-echo techniques using low flip-angle pulses), still the number of resulting images, and the manner in which they can be displayed, do not afford any meaningfully, feasible or practical NMR images for use in a medical screening application for examining an entire or substantially the entire body of a patient.

The present invention provides a medical screening method for examining persons utilizing nuclear magnetic resonance techniques which is practical and feasible in terms of the scanning times for acquiring NMR image data and the number of images which are required to be reviewed. As one of the primary advantages of the present invention is the ability to obtain and display whole body NMR images, the present invention will be described with respect to production of such images. However, it should be appreciated that the present invention can also be used for producing composite NMR images with respect to less than the entire body of the patient. For example, composite images in accordance with the method of the present invention could be obtained for only the head, neck, chest and torso of a patient, or even only selected portions of such parts of the human body. Additionally, it will also be appreciated that composite images of other than planar regions of the body may be produced. For instance, and as will be described more fully hereinbelow, composite images of various portions of the body can be obtained so as to display parts of the circulatory system of a person, thus providing a convenient and usable technique for medical screening of persons for possible vascular problems, such as blockages in the carotid, cerebral and/or coronary arteries, or even possible blockages in the extremities such as the arms and legs. In such instances, the selected region for which a composite image is produced may not comprise a planar region of the person, but rather, the composite image may be in the nature of a projection image showing selected portions of the body in which the arteries and veins are located.

Figure 4:
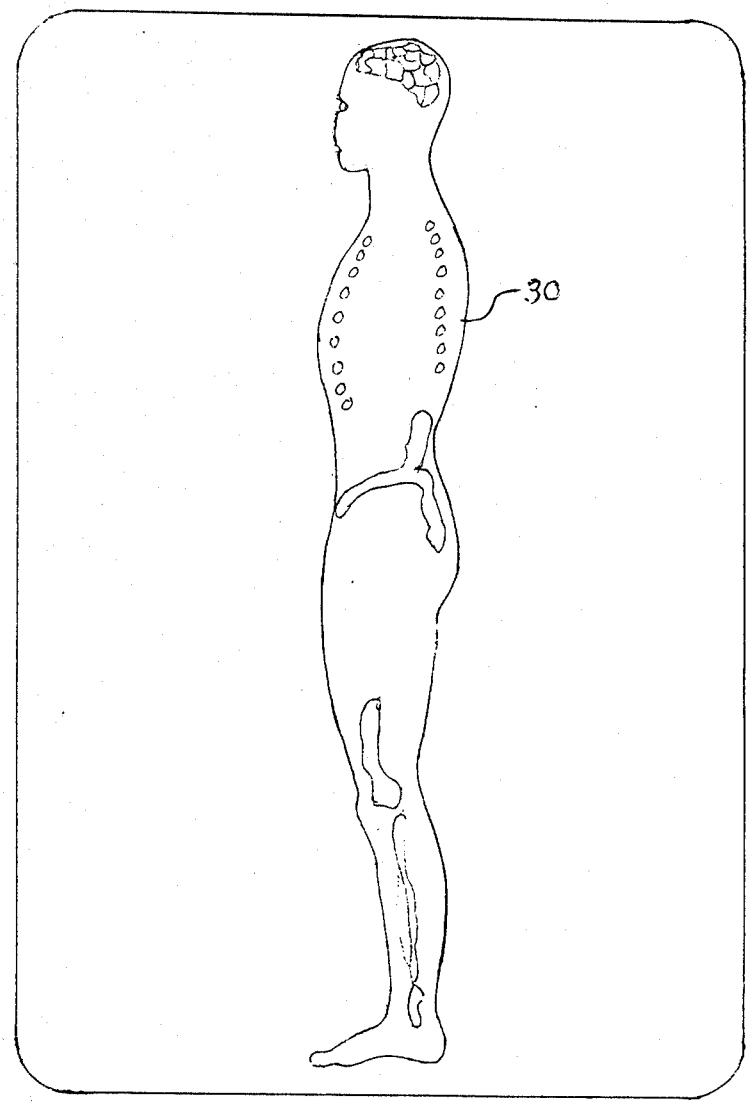
FIG. 4 is a schematic illustration of one type of composite image which can be produced in accordance with the method of the present invention, such composite image representing a composite image along a selected planar region of the person produced by utilizing NMR image data for a substantially planar array of selected region elements which include volume elements contained in a number of different sets of volume elements for which data is acquired.
Figure 5:
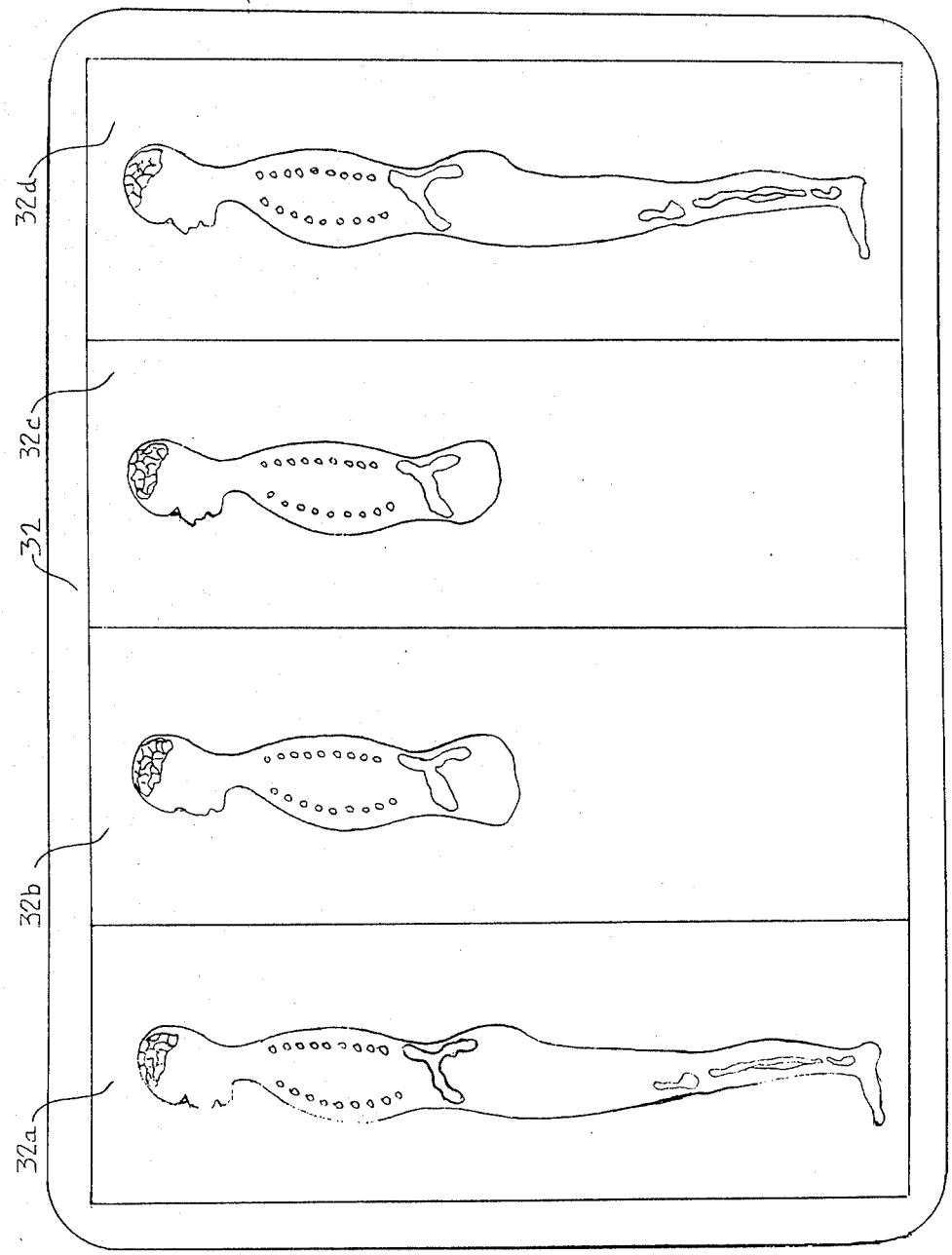
FIG. 5 is a schematic illustration showing a set of four composite images produced in accordance with the present invention being displayed on a monitor, each of the composite images representing a composite image taken along different planar regions of a person.
Figure 6:
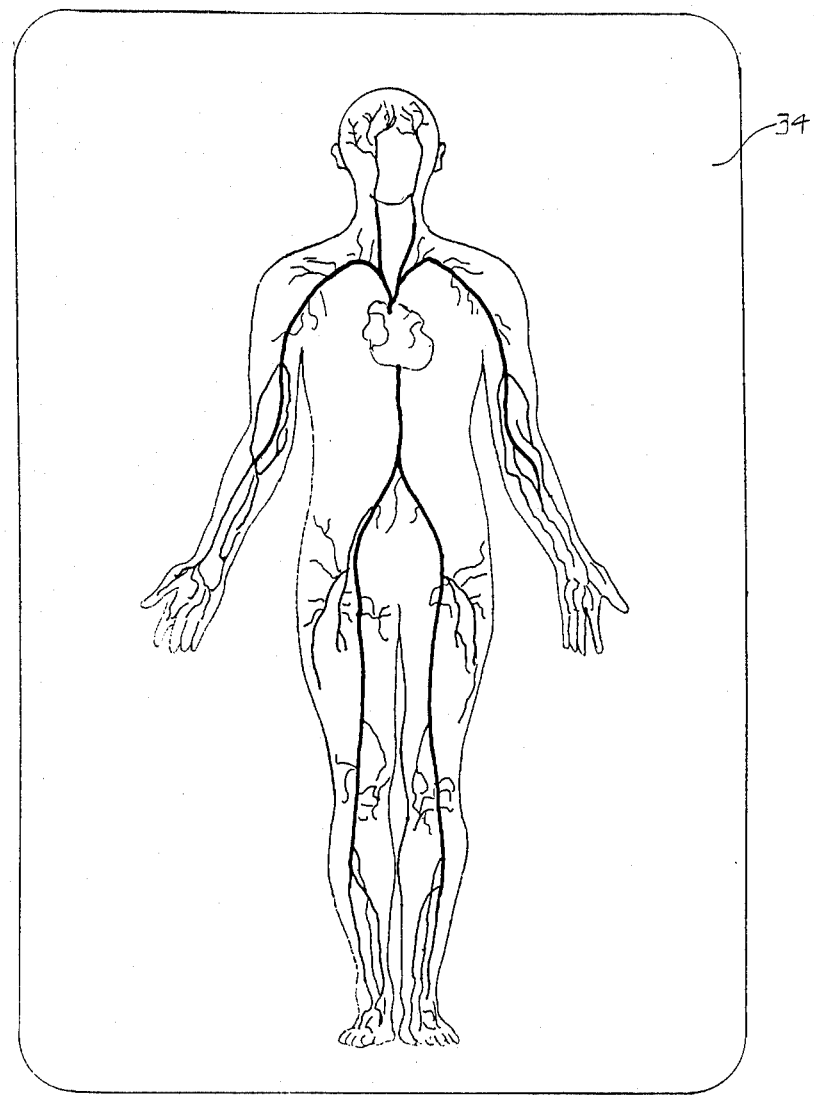
FIG. 6 is another schematic illustration of a different type of composite image which can be produced in accordance with the method of the present invention, such composite image representing a composite image showing a major blood vessels of the circulatory system of a person.

Briefly, and in its broadest aspects, the method in accordance with the present invention comprises positioning a person 24 to be screened in the NMR imaging system 10 so that the scanning volume thereof defines a first volume portion of the person having a first set of volume elements. The system 10 is operated to produce a collection of NMR image data to the first set of volume elements, such collection of NMR image data then being stored, such as in a computer of the NMR imaging system 10. The person 24 is then moved so that the scanning volume of the NMR imaging system 10 defines a second volume portion of the person 24 having a second set of volume elements, and the apparatus 10 then operated to collect and store NMR image data for the second set of volume elements. This procedure of moving or repositioning the person or patient 24 and acquiring NMR image data for sets of volume elements defined by the scanning volume of the NMR imaging system 10 may be repeated as desired so that NMR image data is acquired for a number of volume portions of the person 24. Thereafter, a composite image or images (for example, images 30, 32, 34 as shown in FIGS. 4–6) of the person in a selected region or regions are produced from the collected and stored image data for the various volume portions of the person which have been scanned. The composite images 30, 32, 34 thus may constitute a display of the internal anatomy of the person 24 in a region encompassing several of the various volume portions of the person 24 which have been scanned. The number of such composite images 30, 32, 34 necessary to be reviewed by the physician in order to examine the entire body will thus be significantly fewer in number, thereby affording a feasible, practical and convenient procedure for performing a screening procedure of the person.

As the method in accordance with the present invention contemplates moving the person 24 to reposition different volume portions of the person 24 in the scanning volume, it will be appreciated that it will be necessary to move the patient table 16 a number of times. Accordingly, it is preferred that the patient table 16 be such as to be capable of quickly and precisely positioning or repositioning the person 24 with respect to the scanning volume of the NMR imaging system 10. Such a patient table 16 may comprise the patient table disclosed in copending application Ser. No. 935,207, entitled "Air Flotation Patient Bed", filed concurrently herewith in the names of V. Di Massimo and M. Gelbien, such concurrently filed application hereby being incorporated by reference as though fully set forth hereinafter. Briefly, as disclosed in such copending application Ser. No. 935,207, the patient table 16 comprises a floating bed-type table on which the patient 24 lies and which is guided into the axially extending opening of the NMR imaging system 10, suitable drive mechanisms and controls being provided for enabling precise incremental movement of the table 16, and thus the patient 24 lying thereon, relative to the scanning volume region.

Further, as the scanning volume region of the NMR imaging system 10 remains in a fixed position within the apparatus 10 and is of a predetermined volumetric size, it will be appreciated that the scanning volume region defines the volume portion of the person 24 for which NMR imaging data is to be acquired during a scanning operation. Thus, in positioning a person 24 for each of the scanning operations, all that is necessary is to know the size and location of the scanning volume within the NMR imaging system 10. Furthermore, as noted above, the size of the scanning volume region and the number and size of the set of volume elements for which NMR data is to be collected is, in part, determined by the operating parameters for the imaging technique employed, for example, the nature of the acquisition techniques (for example, single or multiple slices, or three-dimensional volume acquisition techniques), the nature of the magnetic field gradients, the band width of the frequency at which the oscillating or RF field is applied, and the type of NMR signal information to be obtained (for example, $T_1$-weighted or $T_2$-weighted NMR information, calculated $T_1$ and $T_2$ values, or blood flow information). Such operating parameters, as well as the size and location of the scanning volume region and number and size of the set of volume elements for which data will be collected, are known parameters for the imaging technique employed.

In accordance with a preferred embodiment, a person 24 to be screened is initially placed on the patient table 16 and the table 16 then moved into the opening 14 provided in the NMR imaging apparatus 10 so that a first volume portion of the person 24 will be positioned in the scanning volume of the apparatus 10. For instance, this first volume portion may comprise a 3" slice of the upper part of the head, i.e. from the top of the scalp down to a level just above the eyes. The NMR imaging apparatus 10 is then operated to conduct a scanning operation or operations, without moving the person 24, to acquire NMR image data for a three-dimensional set of volume elements within the scanning volume. This can be accomplished utilizing a multi-slice acquisition technique or a series of single-slice acquisition techniques, one after the other, by changing magnetic field gradients and/or the frequency of the applied RF field. In this regard, assuming that the image acquisition technique is controlled so that the volume elements are small cubes approximately 4 mm. along each edge, and that image data is acquired for 20 slices in a 128×128 planar array, the first volume portion of the person will comprise a rectangular solid array of approximately 20"×20"×3".

The resulting image data for the set of volume elements in the first volume portion is then stored in an appropriate storage means, for example, a computer, and the person 24 advanced in the axial direction an appropriate amount, namely three inches, so that a different portion of the body may be scanned in a similar manner. This procedure of advancing the person 24 a selected amount, acquiring NMR image data for three-dimensional sets of volume elements and storing of the data in an appropriate storage means, is then continued until image data is acquired for the entire volume of the body of the person 24. In this regard, FIG. 2 illustrates schematically the series of volume portions 40 for which data is acquired in the manner as described hereinabove. The regions between each of the lines 42 shown in FIG. 2 represent the thickness of the volume portions 40 of the person 24 for which image data is acquired in a single scanning operation as described hereinabove. In terms of the example set forth above, each such volume portion 40 is approximately 3" thick and represents twenty 4 mm. slices or planes for which NMR image data is collected, with each slice containing 128 volume elements across and 128 volume elements deep. From FIG. 2, it will thus be appreciated that approximately twenty-four different volume portions 40, each three inches in height, are required for a six-foot tall person. The number of volume portions 40 will vary depending on the size of each volume portion 40, in this case along the long axis or Z direction of the person 24. It should be appreciated that slicing of the person 24 can occur axially as shown in FIG. 2, or can occur in sagittal, coronal or oblique directions instead, through the use of conventional NMR imaging techniques.

As the NMR image data for sets of volume elements is generated and collected, it is stored in a manner to define a three-dimensional space 50 of rectangular geometry representative of the person 24, such as illustrated schematically in FIG. 3. This requires that the generated NMR image data for each successive set of volume elements 52 be stored in the appropriate location within the three-dimensional array 50. Conveniently, the location of the volume elements or voxels 52 within the three-dimensional array 50 representative of the person 24 can be defined by specifying the X, Y and Z coordinates thereof. Thus, the three-dimensional array 50 of image data can be stored according to the location of the voxels 52 and the NMR signal information for each such voxel 52. For clarity purposes, in FIG. 3 the number of volume elements or voxels 52 along each of the edges of the array 50 is significantly less than the those for which image data is actually acquired in the example set forth above. For example, assuming 4 mm. cubic voxels 52, the number of voxels 52 actually extending in the Z direction as shown in FIG. 3 for a six-foot tall person would be on the order of 457 (72"×25.4 mm./in. divided by 4 mm.). Similarly, the number of voxels 52 extending in the X direction, assuming a twenty-inch-wide person, would actually be 128, and the number of voxels 52 extending in the Y direction, assuming a twelve-inch thickness, would actually be 76. Of course, different voxel sizes and different numbers of voxels 52 for the three-dimensional array 50 of voxels representing a human body could be utilized.

Once NMR image data for the plurality of volume portions 40 of the person are acquired in the manner as described hereinabove and stored in the memory of the computer, a composite image 30, 32, or 34 along any desired selected region of the person 24 can be produced utilizing the stored NMR image data for the three-dimensional array 50 of voxels 52. For example, if a full planar side or sagittal view of the internal anatomy of the person 24 is desired at a particular location, for instance, through the right side of the person, the operation of the equipment can simply specify the set of coordinates of the three-dimensional array 50 which contain the voxels lying along the center X position with a full dimension in the Y and Z directions as illustrated in FIG. 3. Specifically, the operator would specify (such as by inputting of the appropriate parameter information on the console 18 for the voxel locations) that the composite image be formed from voxels at, for instance, the 5" position in the X direction which extend from the 0" to the 72" position in Z direction and from the 0" to the 12" position in the Y direction, i.e. voxels contained in the plane 44 as shown in FIG. 3.

The resulting composite image will then constitute a side or sagittal view of the entire body of the person 24 along a central side plane of the person 24. Such a planar image 30 is illustrated schematically in FIG. 4. In this regard, if the composite image 30 is displayed on a screen, such as the monitor 20 on the operator's console 18, the screen will have to be of sufficient size to accommodate the number of picture elements for which data is to be displayed. For instance, with respect to the example noted above, in which the composite image 30 for a side or saggital view will have approximately 76 pixels horizontally and 457 pixels vertically, such image may conveniently be displayed on a 512 screen capable of displaying a matrix comprised of 640 picture elements across and 512 picture elements down. Indeed, a set 32 of four composite images, for example, images 32a, 32b, 32c, 32d, could be displayed on the monitor 20 as illustrated in FIG. 5, for four different slices or locations within the body.

The NMR signal information acquired for the various volume elements 52 from the various volume portions 40 of the person 24 may comprise any of the conventional NMR signal information conventionally utilized in NMR imaging. As noted hereinabove, in many NMR imaging applications, the NMR signal information constitutes the amplitude or intensity of the generated NMR signals, which in turn is a complex function the spin density of selected nuclei and the $T_1$ and $T_2$ relaxation times. Thus, the NMR amplitude signal information is dependent on the $T_1$ and $T_2$ parameters of the particular tissue from which the NMR signals are generated. The $T_1$ and $T_2$ information contained in the NMR signals, as noted above, is generally indicative of the differences between healthy tissue and diseased or abnormal tissue. Various imaging techniques are also known for emphasizing the relative contributions to the NMR signals of the various tissue related parameters, e.g. $T_1$-weighted and $T_2$-weighted imaging data. Other imaging techniques are also known for calculating actual $T_1$ and/or $T_2$ values. All of these imaging techniques employed in connection with conventional NMR imaging can also be employed in the practice of the method of the present invention.

Further in accordance with the present invention, composite images may be produced for a slice or planar selected region which is several voxels thick, thus minimizing the number of images which would be required to be examined by a physician in order to conduct a complete screen of the entire body of a person 24. Such composite images can be produced by producing average NMR image data for the respective voxels contained in two or more adjacent slices. This is accomplished by averaging the NMR signal information for the sets of adjacent voxels lying in the desired region. For example, if a two-voxel-thick side or sagittal image 30 is desired at a particular pair of X coordinates, say X=a and X=b in FIG. 3, for each Y and Z coordinate the NMR signal information for the two voxels having X coordinates of "a" and "b" will be averaged to produce an average NMR signal value. Such average NMR signal values can then be used to produce the desired composite image 30. With the example given above in which the voxels are of a size of 4 mm. on an edge, each sagittal or side view would then represent a sagittal or side view having a slice thickness of 8 mm. Of course, this same procedure of obtaining average NMR image data can be used with respect to more than two adjacent voxels, as well as with respect to sets of voxels extending in more than one direction. Thus, average NMR image data could be obtained for a cubic array of eight voxels, i.e. sets of adjacent voxels in the X, Y and Z directions.

It will thus be appreciated that composite images 30, 32 along any planar region can be produced from the three-dimensional data array of NMR image data by simply determining the appropriate voxels 52 within the three-dimensional array 50 of voxels for which image data is to be utilized. This can be done for various planar images in the nature of side of sagittal views, or for various planar images in the nature of front or coronal views. For example, the selected region for which the composite image is to be made could be specified as all voxels having a specified X coordinate or a specified Y coordinate.

Also, the three-dimensional data array 50 can be used for providing planar images at selected angles or at different orientations by providing suitable software for selection of the various sets of voxels from which the composite image is to be produced. With respect to such angled or oblique planar images, the selection of the appropriate voxels can be accomplished by specifying the spatial locations of the various voxels which are to be used in producing the composite image. For example, constructing a composite image at a particular angle can be accomplished by actually specifying the set of X, Y and Z coordinates for each voxel 52 which is to be used, or more simply, by specifying the coordinates for a starting voxel and the angle of the desired plane relative to one or more of the axes, using conventional techniques for producing obliquely oriented images.

It will thus be appreciated that the composite NMR images 30, 32 produced in accordance with the present invention, which incorporate image data obtained from a number of different volume portions 40 of a person 24 in a number of different scanning operations, enable a physician to screen the entire body of the person 24, or a significantly large volume portion of the patient's body, in a relatively convenient and practical manner. In particular, the number of such composite images 30, 32 which must be reviewed are significantly less than would otherwise be required if conventional NMR images were produced. Furthermore, although in the preferred embodiment, NMR image data is acquired for the entire body from which full-view images of all portions of the body can be produced, in some instances, it may be sufficient to acquire NMR image data for less than the entire body of the person 24. For instance, for some medical screening applications, it may only be necessary to produce composite images of the head, neck, chest and/or torso areas of the body, or even some lesser portion of the body. However, in most medical screening applications, the volume portions 40 for which NMR image data will be acquired will be on the order of at least half the height of the person 24.

Also, since the method in accordance with the present invention is to be used for screening of a patient, it will be appreciated that high resolution NMR images are not as important, as they otherwise would be if a physician were examining a particular area of the body for determining whether a particular abnormality or abnormalities are present. That is, for screening applications were the physician is not locating or examining for a particular problem, but rather, is conducting a screen on asymptomatic persons for all types of abnormalities to hopefully detect diseases or illnesses at an early state in their development, generally lower resolution images will be sufficient. If any suspected or possible abnormality is detected on the composite images 30, 32, further high resolution images can be obtained for a particular area or region of interest in further scanning operations. This can very easily be accomplished while the person 24 remains in the NMR imaging apparatus 10. That is, after acquisition of NMR image data for a number of separate volume portions 40 of the patient, e.g. for substantially the entire body of the person 24, composite NMR images 30, 32 can be produced and reviewed by the physician while the person 24 remains in the apparatus 10, for instance by being displayed on the monitor 20. If the physician detects an abnormality or suspected abnormality on any of the composite images 30, 32, a high resolution scan of the particular area or region of interest of the person 24 can be performed by repositioning the table 16 having the person 24 thereon without having to recall the person at a later time. Here it should be appreciated that the use of lower resolution images for screening applications, based on larger-sized voxels, means that a lower number of images must be reviewed initially in order to perform a screen of the person 24. This factor is important in providing a convenient and useful screening procedure based upon NMR images. Preferably, the voxel size represented in the composite images 30, 32 is on the order of 2–10 mm along an edge for rectangular-shaped voxels. Of course, other shaped voxels could be used, as well as larger or smaller-sized voxels, depending on the particular screening procedure.

Further in accordance with the present invention, preferably the NMR data acquisition operations are performed at a relatively high speed in order to minimize the data acquisition time. In part, such rapid scanning sequences can be obtained by utilizing larger-sized voxels or volume elements for which NMR image data is to be acquired, and/or by utilizing other pulsing sequences which have as their aim the rapid acquisition of NMR image data. For example, there has recently been developed several new NMR imaging techniques known as field or gradient echo-scanning techniques which utilize low flip-angle pulses, i.e. RF pulses which rotate the net magnetization of the nuclei through a small angle, significantly less than 90°. Examples of such rapid image data acquisition techniques are described, for example, in the article entitled "Flash Imaging. Rapid NMR Imaging Using Low Flip-Angle Pulses" by A. Haase et al, appearing in the *Journal of Magnetic Resonance* 67, 258–266 (1986) and in the article entitled "Technical Note: Rapid Three-Dimensional MR Imaging Using Flash Technique" by Frahm et al, appearing in the *Journal of Computer-Assisted Tomography* 10(2):363–368, March/April, 1986, both of which articles are only hereby incorporated by reference as though fully set forth herein. The acquisition technique described in the first-mentioned article is capable of producing a 128×128 pixel image, having 1 mm. resolution with 4 mm. slice thickness, in approximately 2.3 seconds. The other article mentioned above is directed to a three-dimensional volume acquisition technique for acquiring image data for a 128×128×128 three-dimensional volume, having 1 mm. resolution with slice thickness of 1 mm., in approximately four minutes.

Utilizing a 128-level field or gradient echo technique such as disclosed in the first-mentioned article in the method of the present invention for voxel sizes of 4 mm. on an edge, image data for a single slice can be obtained in approximately 2.3 seconds. Thus, for image data to be acquired for approximately 457 axial slices (corresponding to a six-foot tall patient), and with repositioning of the person 24 for each scanning sequence being accomplished in approximately an average of 0.2 seconds for each slice, a person can be scanned from top to bottom and NMR image data acquired therefor in under twenty minutes. This is a reasonable and practical time for acquisition of NMR image information for the entire body of the person from which a physician can then produce particular composite images 30, 32 in order to screen the patient for possible disease. Of course, the number of slices (and thus, the scanning time) could be different if the slices are taken in a different direction, e.g. along the X or Y directions.

Further in accordance with the present invention, techniques other than specifying particular sets of voxels 52 can be employed in determining the selected region for which the composite NMR image is to be constructed. For example, instead of specifying particular sets of voxels 52 in the three-dimensional rectangular geometric array 50 of data, the selection of the voxels 52 to be included in the desired composite image can be based upon the signal information obtained for the voxels. In particular, in accordance with another embodiment of the present invention, composite images 30 could be produced of those voxels for which the NMR signal information is representative of blood flow, thereby producing a composite image 34 displaying portions or parts of the blood circulatory system of the person 24. This can be achieved in accordance with the present invention by utilizing a scanning technique in which the NMR signal information for any voxel 52 in which there is blood flow has a value above (or, in some instances, below) a predetermined value, and then producing a composite image 34 only from those voxels in which the NMR signal information is above the predetermined level.

More particularly, the article entitled "Projection Angiograms of Blood Labeled by Adiabatic Fast Passage", appearing in *Magnetic Resonance In Medicine* 3, 454–462 (1986) by W. Thomas Dixon, et al, which is hereby incorporated by reference, describes an NMR image data acquisition procedure by which the NMR signal information for particular voxel elements encompassing blood flow appear as "white" or bright on the displayed image produced from such signal information. Other NMR signal information representative of static or stationary components within the voxel elements appear dark or black on the image. As NMR images are merely visual translations of NMR intensity values for the particular pixels being displayed, it will be appreciated that high signal amplitude values (corresponding to white or brightness on images) are indicative of blood flow such as occurs in the arteries and veins of the circulatory system. Thus, in order to produce a composite image 34 of parts of the arterial and/or venous regions of the body, all that need be done is to perform a selection process based upon the amplitude of the NMR signal information. In other words, the selected region for which a composite image 34 is to be produced can be determined by only selecting and utilizing those voxels 52 within the three-dimensional geometric rectangular array 50 in which the signal information is above a predetermined value. As those voxels 52 within the three-dimensional array 50 in which there is blood flow will have high-amplitude values, the resulting composite image 34 will constitute an image of parts of the circulatory system of the person 24.

Here, it should be noted that the various regions encompassing the circulatory system are located at different depths or Y coordinates in the three-dimensional array 50. Thus, the resulting composite image 34 based on a signal amplitude selection technique will have voxels located at different Y positions, and accordingly, will be in the nature of a projection-type image showing or displaying portions of the circulatory system of the person 24 in a single composite image 34. This is illustrated, for example, in the schematic composite image 34 shown in FIG. 6. Of course, a signal amplitude selection technique could be combined with a spatial selection technique if greater clarity is desired. Also, the composite image 34 can be one in which the high amplitude NMR signal information is displayed as "white" or bright, or can be one in which the high-amplitude NMR signal amplitude is displayed as "black" or dark, using a reverse contrast procedure. For clarity, the composite image 34 shown in FIG. 6 is one in which blood flow is displayed as black or dark.

This technique for displaying part of a patient's circulatory system can have powerful applications in screening of patients for various vascular diseases, such as hardening of the arteries, aneurysms, etc., at a very early stage in the development of such diseases. In particular, with the method of the present invention, a physician may obtain composite circulatory images 34 of a patient on a regular basis to determine the existence or worsening of any potential circulatory or vascular diseases. Here it should be noted that approximately 90% of the deaths involving vascular-type diseases occur in connection with the cerebral, carotid and coronary arteries. Thus, the medical screening technique of the present invention in which composite images can be obtained in a rapid manner for examination of the cerebral, carotid and/or coronary arteries, is particularly useful for screening of patients for the early detection of arterial disease or vascular problems in general.

Of course, the medical screening method of the present invention also has powerful application with respect to a wide variety of other types of diseases or illnesses, such as cancer, multiple sclerosis, inflammation, hemorrhage, trauma, arthritis, heart attacks, strokes, etc. Indeed, the screening method of the present invention can be used for screening of all abnormalities for which NMR imaging techniques have proven useful.

As will be appreciated from the description above, with the present invention, NMR image data can be acquired relatively rapidly and displayed in a useful and practical manner to enable a physician to conduct a rapid screen of a person 24 by simply viewing a limited number of composite images 30, 32, 34. In particular, with the method in accordance with the present invention, composite images 30, 32, 34 can be obtained for virtually the entire body of the person 24, thus enabling the physician to examine a limited number of images in order to be able to view virtually any portion of the body for the early detection of disease or illness. It is no longer necessary that NMR imaging applications be confined to only examining particular suspected regions of interest; rather, the region of interest becomes the entire body of the patient. This will take NMR imaging out of the realm of only examining the unhealthy or suspected unhealthy patients, and instead enable physicians to conduct rapid screens with respect to all persons. As a result, people will now be able to be screened using NMR techniques and principles in a rapid, non-time-consuming procedure and hopefully obtain a clean bill of health within the limitation of MRI and its applications as set forth herein, or at least learn of any potential diseases or illnesses at an early stage when they can easily be treated or potential risk minimized by preventive care.

Thus, in accordance with the present invention, there is provided a medical screening method for examining a person 24 which comprises the steps of providing an NMR apparatus 10 having a scanning volume region into which a part of a person to be examined is positioned and also having NMR imaging means operable to produce a collection of spatially encoded NMR image data for a set of volume elements from the part of the person positioned in the scanning volume region. The NMR imaging means is operable to produce the collection of spatially-encoded NMR image data relative to the scanning volume region during the course of a single scanning operation. Also, the collection of spatially-encoded NMR image data includes NMR signal information and spatial information for the set of volume elements. The method of the present invention involves positioning a person 24 within the NMR apparatus 10 so that the scanning volume region defines a first volume portion 40 of the person 24 having a first set of volume elements 52, and then operating the NMR imaging means to conduct a scanning operation to produce the collection of NMR image data for the first set of volume elements 52. The collected NMR image data for the first set of volume elements 52 is then stored, and the person 24 moved so that the scanning volume region defines an additional volume portion 40 of the patient having an additional set of volume elements 52, the additional portion of the patient and additional set of volume elements 52 being different from the first volume portion and first set of volume elements 52. The operating and storing steps are then repeated for each additional volume portion 40 of the person 24 defined by the scanning volume region so as to produce and store the collections of NMR image data for each of the additional sets of the volume elements 52. After data has been acquired for the desired volume portions 40 of the person 24, a composite NMR image 30, 32, 34 of the person 24 in a selected region, contained within parts of the volume portions 40 of the person 24 for which data has been acquired, is then produced from the stored collection of NMR image data. The selected region for which the composite image 30, 32, 34 is produced is comprised of an array of selected region elements which are contained in the selected region of the person 34, the selected region elements including volume elements contained in the first set of volume elements 52 and volume elements contained in at least one additional set of volume elements 52.

Further, in accordance with the present invention, the selection of the desired region to be displayed in the composite image 30, 32, 34 can be made on the basis of selected volume elements 52 for which NMR image data has been collected and/or on the basis of the NMR signal information contained in the collection of NMR image data. An example of the former selection process comprises various planar images 30, 32 of the person 24 along selected planar regions, whereas an example of the latter is a composite NMR image 34 of parts of the circulatory system in which the selection is made on the basis of volume elements 52 having NMR signal information representative of blood flow. Of course, other selection techniques can be employed for selecting the voxels from which the composite image is to be produced.

Still further, in accordance with the present invention, the composite image 30, 32, 34 is produced and reviewed by a physician, for example, by being displayed in the monitor 20 of the console 18, while the person 24 remains in the NMR imaging apparatus. If any abnormalities or possible abnormalities are detected as a result of the review of the composite image 30, 32, 34, a high-resolution NMR image or sets of images in the particular region of interest can be obtained. Thus, in accordance with this technique, the NMR screening operation serves to locate particular regions of interest for further and subsequent examination while the person 24 remains in the apparatus, thus minimizing the inconvenience to the person 24 which would otherwise occur by having a series of scans done at different times.

A latitude of modification, change and substitution is intended in the foregoing disclosure, and in some instances, some features of the invention will be employed without a corresponding use of other features. Accordingly, it is appropriate that the appended claims be constructed broadly in a manner consistent with the spirit and scope of the invention herein.

What is claimed is:

1. A medical screening method for examining a patient comprising the steps of:

providing an NMR apparatus having a scanning volume region into which a part of a person to be examined is positioned and having NMR imaging means operable to produce a collection of spatially encoded NMR image data for a set of volume elements from said part of said person positioned in said scanning volume region, said NMR imaging means being operable to produce said collection of spatially encoded NMR image data relative to said scanning volume region during the course of a single scanning operation and said collection of spatially encoded NMR image data including spatial information and NMR signal information for said set of volume elements;

positioning a patient within said NMR apparatus so that said scanning volume region defines a first volume portion of said patient having a first set of volume elements;

operating said NMR imaging means to conduct a scanning operation to produce said collection of NMR image data for said first set of volume elements;

storing said collection of NMR image data for said first set of volume elements;

moving said patient so that said scanning volume region defines at least one additional volume portion of said patient having at least one additional set of volume elements, said at least one additional set of volume elements being different from said first set of volume elements;

repeating said operating and storing steps for said at least one additional volume portion of said patient defined by said scanning volume region so as to produce and store said collection of NMR image data for said at least one additional set of volume of elements;

selecting an array of selected region elements from said volume elements of said sets of volume elements so that said array of selected region elements is representative of a selected region of said patient contained within parts of said first and said at least one additional volume portions of said patient, said array of selected region elements including volume elements contained in said first set of volume elements and volume elements contained in said at least one additional set of volume elements, but consisting of less than all of said volume elements of said sets of volume elements; and producing from said stored collections of NMR image data a composite image of said patient in said selected region of said patient by utilizing said spatially encoded NMR image data which corresponds to said array of selected region elements.

2. The method of claim 1 wherein said step of moving said patient comprises moving said patient a plurality of times so that said scanning volume region defines a plurality of additional volume portions of said patient having a plurality of additional sets of volume elements, each of said additional sets of volume elements being different from said first set of volume elements and different from each other of said additional sets of volume elements; wherein said operating and storing steps are repeated for each of said additional volume portions of said patient after movement of said patient; and wherein said step of selecting comprises selecting an array of selected region elements which include volume elements contained in said first set of volume elements and volume elements contained in said additional sets of volume elements so that said selected region of said patient is contained within parts of said first and said additional volume portions of said patient.

3. The method of claim 2 wherein said steps of positioning and moving said patient comprise positioning and moving said patient relative to said scanning volume region of said NMR apparatus so that said scanning volume region defines a plurality of adjacent volume portions of said patient and wherein said selected region of said patient comprises a substantially planar region extending transverse to said adjacent volume portions.

4. The method of claim 3 wherein said plurality of adjacent volume portions include volume portions of said patient's head, neck, chest and torso.

5. The method of claim 4 wherein said plurality of adjacent volume portions further include the extremities of said patient.

6. The method of claim 3 wherein said plurality of adjacent volume portions comprise a plurality of axially-arranged adjacent volume portions.

7. The method of claim 6 wherein the dimension of said scanning volume region in the axial direction is about 12" or less, and wherein said plurality of axially-arranged adjacent volume portions extend along a distance of at least three feet.

8. The method of claim 6 wherein said plurality of axially-arranged adjacent volume portions extend over a distance approximately equal to one half of the height of said patient.

9. The method of claim 2 wherein said steps of positioning and moving said patient comprise positioning and moving said patient relative to said scanning volume region of said NMR apparatus so that said first and additional sets of volume elements define a plurality of adjacent planar arrays of volume elements.

10. The method of claim 9 wherein said plurality of adjacent planar arrays of volume elements comprise a plurality of axially-arranged planar arrays of volume elements.

11. The method of claim 9 wherein said plurality of adjacent planar arrays of volume elements comprise a plurality of sagittally-arranged planar arrays of volume elements.

12. The method of claim 9 wherein said plurality of adjacent planar arrays of volume elements comprise a plurality of coronally-arranged planar arrays of volume elements.

13. The method of claim 9 wherein said plurality of adjacent planar arrays of volume elements comprising a plurality of obliquely-arranged planar arrays of volume elements.

14. The method of claim 1 wherein said provided NMR apparatus includes a movable table on which a patient is positioned, said movable table being movable relative to said scanning volume region of said NMR apparatus to position a selected part of a patient to be examined in said scanning volume region; and wherein said step of positioning comprises moving said table to a first position within said NMR apparatus and wherein said step of moving said patient comprises moving said table to an additional position within said NMR apparatus which is different from said first position.

15. The method of claim 1 wherein said step of moving said patient comprises moving said patient to a position within said NMR apparatus so that said at least one additional volume portion is adjacent to said first volume portion of said patient.

16. The method of claim 1 wherein each of said selected region elements comprises a composite element which includes at least two of said volume elements of said sets of volume elements; and wherein said step of producing a composite image comprises averaging NMR image data for said at least two volume elements which comprise each of said composite elements to obtain average NMR image data for said composite elements, and then producing said composite image of said patient using said average NMR imaging data for said composite elements.

17. The method of claim 1 wherein said NMR signal information included in said collection of spatially encoded NMR image data comprise $T_1$ and $T_2$ NMR information for said sets of volume elements.

18. The method of claim 1 wherein said step of selecting comprises selecting said selected region elements based upon said NMR signal information contained in said stored collections of NMR image data.

19. The method of claim 1 wherein said step of selecting comprises selecting said selected region elements based upon said spatial information contained in said stored collections of said NMR image data.

20. The method of claim 1 wherein said steps of operating said NMR imaging means comprise operating said NMR imaging means to conduct a multi-slice scanning operation with respect to said volume portions of said patient defined by said scanning volume region.

21. The method of claim 1 wherein said step of operating said NMR imaging means comprises operating said NMR imaging means to conduct a three-dimensional volumetric scanning operation for said volume portions of said patient defined by said scanning volume region.

22. The method of claim 1 wherein said selected region comprises a selected planar region of said patient contained within said first and said at least one additional volume portions of said patient, said selected planar region being comprised of a substantially planar array of selected region elements contained in said selected planar region.

23. The method of claim 1 wherein said selected region includes parts of the blood circulatory system of said patient so that said composite image represents an image of a part of the circulatory system of said patient.

24. The method of claim 23 wherein said step of selecting comprises selecting said selected region elements based upon NMR signal information which is representative of blood flow.

25. The method of claim 23 wherein said steps of operating said NMR imaging means comprise operating said NMR imaging means so that said NMR image data includes NMR signal information representative of blood flow in said sets of volume elements, and wherein said step of selecting comprises selecting said selected region elements so that said selected region is a region which exhibits blood flow.

26. The method of claim 23 wherein said selected region of said patient is a region which includes at least one of the three arterial regions consisting of the carotid, coronary and cerebral arterial regions of said patient.

27. The method of claim 26 wherein said selected region of said patient is a region which includes at least two of said three arterial regions consisting of said carotid, coronary and cerebral arterial regions.

28. The method of claim 23 wherein said selected region of said patient is a region which includes the venous region of said patient.

* * * * *